(12) United States Patent
Gorek (10) Patent No.: US 6,752,809 B2
(45) Date of Patent: Jun. 22, 2004

(54) SYSTEM AND METHOD FOR REINFORCING BONE IN PREPARATION FOR SCREW IMPLANTATION

(75) Inventor: Josef E. Gorek, Larkspur, CA (US)

(73) Assignee: K2 Medical, LLC, Herndon, VA (US)

(*) Notice: Subject to any disclaimer, the term of this patent is extended or adjusted under 35 U.S.C. 154(b) by 198 days.

(21) Appl. No.: 10/004,043

(22) Filed: Dec. 4, 2001

(65) Prior Publication Data

US 2003/0105468 A1 Jun. 5, 2003

(51) Int. Cl.[7] .............................................. A61B 17/58
(52) U.S. Cl. ....................................................... 606/92
(58) Field of Search ............................. 606/92, 93, 94; 604/187

(56) References Cited

U.S. PATENT DOCUMENTS 4,653,487 A * 3/1987 Maale .......................... 606/62
6,241,734 B1 * 6/2001 Scribner et al. ............... 606/93
2002/0032447 A1 * 3/2002 Weikel et al. ................. 606/86
2003/0036763 A1 * 2/2003 Bhatnagar et al. ............. 606/94
2003/0105469 A1 * 6/2003 Karmon ........................ 606/92

* cited by examiner

Primary Examiner—Eduardo C. Robert
(74) Attorney, Agent, or Firm—Piper Rudnick, LLP; Perry E. Van Over (57) ABSTRACT

A system and method for reinforcing bone in preparation for screw implantation. One system embodiment comprises a threaded and centrally bored cannula with a perforated distal end, a cannula applicator frictionally fitting within the central bore, a plunger translating within the central bore (the plunger having a internal longitudinal guide wire), bone cement, and a cannulated drill bit. One method embodiment comprises drilling and tapping a hole in a vertebral body, inserting the applicator into the central bore, screwing the cannula into the tapped hole by rotating the applicator, removing the applicator, injecting the bone cement into the central bore, distributing the bone cement out the holes in the distal end of the cannula and into the surrounding bone using the plunger, letting the bone cement harden, and drilling out the plunger using the cannulated drill following the guide wire.

20 Claims, 8 Drawing Sheets

SYSTEM AND METHOD FOR REINFORCING BONE IN PREPARATION FOR SCREW IMPLANTATION

FIELD OF THE INVENTION

This invention relates generally to a bone reinforcement process and surgical tool for, and more particularly, the present invention relates to an application device for injecting poly methyl methacrylate into a bone matrix through a canulated element through which a screw may subsequently be inserted.

BACKGROUND OF THE INVENTION

The bones and connective tissue of an adult human spinal column consists of an upper portion having more than 20 discrete bones, and a lower portion which consists of the sacral bone and the coccygeal bodies. The bones of the upper portion are generally similar in shape, however, they do vary substantially in size in accordance with their individual position along the column and are, therefore, anatomically categorized as being members of one of three classifications: cervical, thoracic, or lumbar.

These similarly shaped bones vary in size, but are each similarly coupled to the next by a tri-joint complex. The trijoint complex consists of an anterior disc and the two posterior facet joints, the anterior discs of adjacent bones being cushioned by cartilage spacers referred to as intervertebral discs. The posterior portion of the vertebral bone is coupled to the anterior portion by a pair of bone bridges referred to as pedicles, between which the spinal canal is housed.

In its entirety, the spinal column is highly complex in that it houses and protects critical elements of the nervous system which have innumerable peripheral nerves and arterial and veinous bodies in close proximity. In spite of these complexities, the spine is a highly flexible structure, capable of a high degree of curvature and twist through a wide range of motion.

Genetic or developmental irregularities, trauma, chronic stress, tumors, and disease, however, can result in spinal pathologies which either limit this range of motion, or which threaten the critical elements of the nervous system housed within the spinal column. A variety of systems have been disclosed in the art which achieve this immobilization by implanting artificial assemblies in or on the spinal column. These assemblies may be classified as anterior, posterior, or lateral implants. As the classification suggests, posterior implants are attached to the back of the spinal column, generally hooking under the lamina and entering into the central canal, attaching to the transverse process, or coupling through the pedicle bone. Lateral and anterior assemblies are coupled to the vertebral bodies.

The region of the back which needs to be immobilized, as well as the individual patient's anatomy, determine the appropriate surgical protocol and implantation assembly. Because the spine is routinely subject to high loads which cycle during movement, primary concerns of physicians performing spinal implantation surgeries focus on screw pull-out and screw failure. Screw pull-out occurs when the cylindrical portion of the bone which surrounds the inserted screw fails. Screw pull-out often an additional danger in that it often leaves the bone into which the screw was implanted completely useless with respect to continued implant support. This is especially true when the patient suffers from osteoporosis. In such patients the bone matter is often much less structurally supportive and lacks the necessary holding strength to prevent macromotion of the screws which may be implanted therein, thus severely limiting the immobilization potential of the assembly.

The use of artificial materials, such as bone cements and specific organic bone mimicking compounds such as poly methy methacrylate (PMMA), have been taught in the art as being effective in strengthening the osteoporotic bones to effect better immobilization of the screws. Percutaneous insertion of bone reinforcing agents has been successful in many instances, and is generally known as vertebroplasty. This "closed" use of PMMA and/or bone cement is useful in supporting subsiding bone masses in some instances, but is insufficient in those cases in which pedicle screw support is required. One of the failings of vertebralplasty, however, is that the cured PMMA/bone cement is often so much more dense and hard than the surrounding natural bone material that if subsequent screws need to be inserted, the bone drill is confounded by the difference in material properties.

The "open" use of PMMA and/or bone cement has been thought of as an alternative to "closed" use, especially when posterior implants are expected to be utilized. In such an instance, the patient's posterior spine is exposed and a bone drill is used to bore a hole through the pedicles for the posterior assembly to be implanted. Prior to the screws being implanted, however, the surgeon injects a quantity of PMMA/bone cement into the hole. Subsequently, the screw is inserted into the hole with the uncured cement. As the cement harden around the threads of the screw, however, the screw becomes thoroughly incarcerated in the hole, and is thus irretrievable. This presents a significant problem for potential revision surgery as well as being a cumbersome and time sensitive process (as the PMMA/bone cement must not dry before the screw is implanted.

It is, therefore, the principal object of the present invention to provide a bone cement injector system for use in spine surgery wherein the surgeon has the ability to assemble the bone cement injectors without the time pressure of inserting the screws exactly after the material has been inserted.

It is also an object of the present invention to provide a bone cement injector system for use in spine surgery wherein the surgeon has the ability to insert the pedicle screws into a dried bone cement cavity which will support, but not incarcerate the screw against removal if necessary.

Other objects of the present invention not explicitly stated will be set forth and will be more clearly understood in conjunction with the descriptions of the preferred embodiments disclosed hereafter.

SUMMARY OF THE INVENTION

The preceding objects are achieved by the present invention, which is a system and method for reinforcing bone in preparation for screw implantation. A system of the invention in one embodiment comprises a threaded cannula having a central bore and a perforated distal end, a cannula applicator that is insertable into the central bore and which achieves a friction fit within the central bore, a plunger that is insertable into the central bore and which achieves an intimate fit within the central bore (the plunger having a guide wire passing through its central longitudinal axis), bone cement, and a cannulated drill bit. A method of the invention in one embodiment comprises drilling and tapping a hole in a vertebral body, inserting the applicator into the central bore of the cannula, screwing the cannula into the tapped hole by rotating the applicator, removing the applicator, injecting the bone cement into the central bore, distributing the bone cement out the holes in the distal end of the cannula and into the surrounding bone using the plunger, letting the bone cement harden, and drilling out the plunger using the cannulated drill following the guide wire. Thereafter, the surgeon can re-tap the hole and insert a bone screw into the reinforced vertebral body.

More particularly, a cannula of the invention has an elongated cylindrical body with a central bore, the body having a proximal end providing access to the bore (especially access by a cannula applicator, plunger, syringe and drill bit of the present invention, as described in greater detail below), and a distal end that is perforated. The outer surface of the cannula is threaded for engagement with threads of a tapped drill hole and to restrict proximal migration of the bone cement, as described in greater detail below. The cannula should be formed from biocompatible material (e.g., poly methyl methacrylate) inasmuch as it will become incarcerated into the target vertebral body in accordance with the procedures described herein. Preferably, the cannula has a radiodense tip that can be used to aid the surgeon in determining the position of the cannula after the cannula has been placed into the target vertebral body.

A cannula applicator of the invention has an elongated cylindrical body and is used to assist the surgeon in threading the cannula into a tapped drill hole and in determining the placement of the cannula in the vertebral body, as described in greater detail below. Accordingly, the applicator is dimensioned so that it can be placed into and removed from the proximal end of the cannula and so that when the applicator is placed into the bore of the cannula, it fits snugly within the bore. The intimate fit enables the applicator to provide structural support for the cannula as the cannula is twisted into the drill hole, and causes the applicator to grip the walls of the bore so that cannula will rotate when the applicator is rotated, so that the cannula will threaded into the drill hole. Preferably, the applicator comprises a radiodense material or is of a radiodense configuration, so that it can be used to determine the position of the cannula as the cannula is threaded into the drill hole.

A plunger of the present invention has an elongated cylindrical body that fits tightly within the bore of the cannula so that it can be used to squeeze bone cement out the holes in the distal end of the cannula as described in greater detail below. Preferably, the body is formed from a material that is softer than the biocompatible material from which the body of the cannula is formed. As described in greater detail below, this difference in material facilitates the drilling away of the plunger after it is used to distribute the bone cement. Also preferably, the plunger is formed from biocompatible material (e.g., poly methyl methacrylate), as some of the plunger may remain after most of the plunger has been drilled away, and the remaining portion would become incarcerated in the vertebral body. Also preferably, the body has a central longitudinal axis and an internal guide wire passing through the central longitudinal axis. As described in greater detail below, this guide wire also facilitates the drilling away of the plunger.

During use of the invention, upon proper preparation of the target vertebral body or bodies in accordance with known and accepted surgical procedures, the surgeon drills a hole in the target vertebral body. Then, the surgeon threads the hole using a tap in a manner known in the art. The surgeon repeats the above procedure for each hole he wishes to drill.

Next, the surgeon inserts into the hole a cannula of the present invention, using an appropriately sized cannula applicator of the present invention. The surgeon inserts the applicator into the proximal end of the cannula and into the bore of the cannula, establishing a tight fit of the applicator against the walls of the bore. Once the applicator is fitted into the bore, the surgeon places the cannula into the tapped hole, and repeatedly turns the applicator to screw the cannula into the hole to the desired position (typically, all the way into the hole). The intimate fit of the applicator in the bore facilitates the rotation of the cannula in response to the rotation of the applicator. The structural integrity of the applicator, in conjunction with the intimate fit of the applicator in the bore, provides structural support for the thin-walled cannula as the cannula is twisted into position. For each drilled hole, the surgeon places a cannula into the drilled hole using an appropriately sized applicator in accordance with the above procedure. The surgeon should leave each applicator in place until it is time to inject the bone cement, as described below. This will keep bleeding to a minimum and will continue to make possible radiographic assessments of the position of each applicator and accordingly each cannula.

Once each drilled hole has been fitted with a cannula, the surgeon prepares the appropriate bone cement mixture and loads one or more syringes with the bone cement, in a manner know in the art. Then, for each installed cannula, one at a time, the surgeon removes the applicator, injects an appropriate amount of the bone cement into the bore using the syringe(s), and applies a plunger of the present invention to distribute the bone cement through the holes of the distal end of the cannula. In order to effect this procedure for each cannula, the surgeon first removes the applicator from the cannula by pulling it from the bore. Next, the surgeon prepares the bone cement, loads the syringe(s), and injects the bone cement into the bore. Then, the surgeon inserts an appropriately sized plunger of the present invention into the distal end of the cannula and into the cannula bore, pushing the plunger down the bore so that the bone cement squeezes out the holes at the distal end of the cannula and into the bone surrounding the cannula. For each cannula, the surgeon leaves the plunger in until each plunger has been applied and the bone cement has set in the surrounding bone. The setting of the bone cement in the surrounding bone strengthens the surrounding bone in preparation for the next steps, which involve re-tapping the target vertebral body for a bone screw.

Once each plunger has been applied and the distributed bone cement has set, the surgeon drills out each plunger using a drill and cannulated drill bit. The surgeon selects a cannulated drill bit having an appropriate outer diameter, sets the drill bit into the drill, passes the drill bit over the guide wire extending from the plunger, and proceeds to drill into the plunger body, following the guide wire to ensure that primarily the plunger body is being drilled away. As noted above, the preferable softness of the plunger body relative to the cannula body facilitates the drilling away of primarily the plunger body. The surgeon repeats this procedure for each installed cannula.

Finally, the surgeon threads each hole that remains after each plunger has been removed, using a tap in a manner known in the art. Once each new hole has been tapped, the surgeon can insert a bone screw of the surgeon's choice into each hole, and complete the operation.

DETAILED DESCRIPTION OF THE PREFERRED EMBODIMENT

While the present invention will be described more fully hereinafter with reference to the accompanying drawings, in which particular embodiments and methods of implantation are shown, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope. Like numbers refer to similar features of like elements throughout.

Figure 1A:
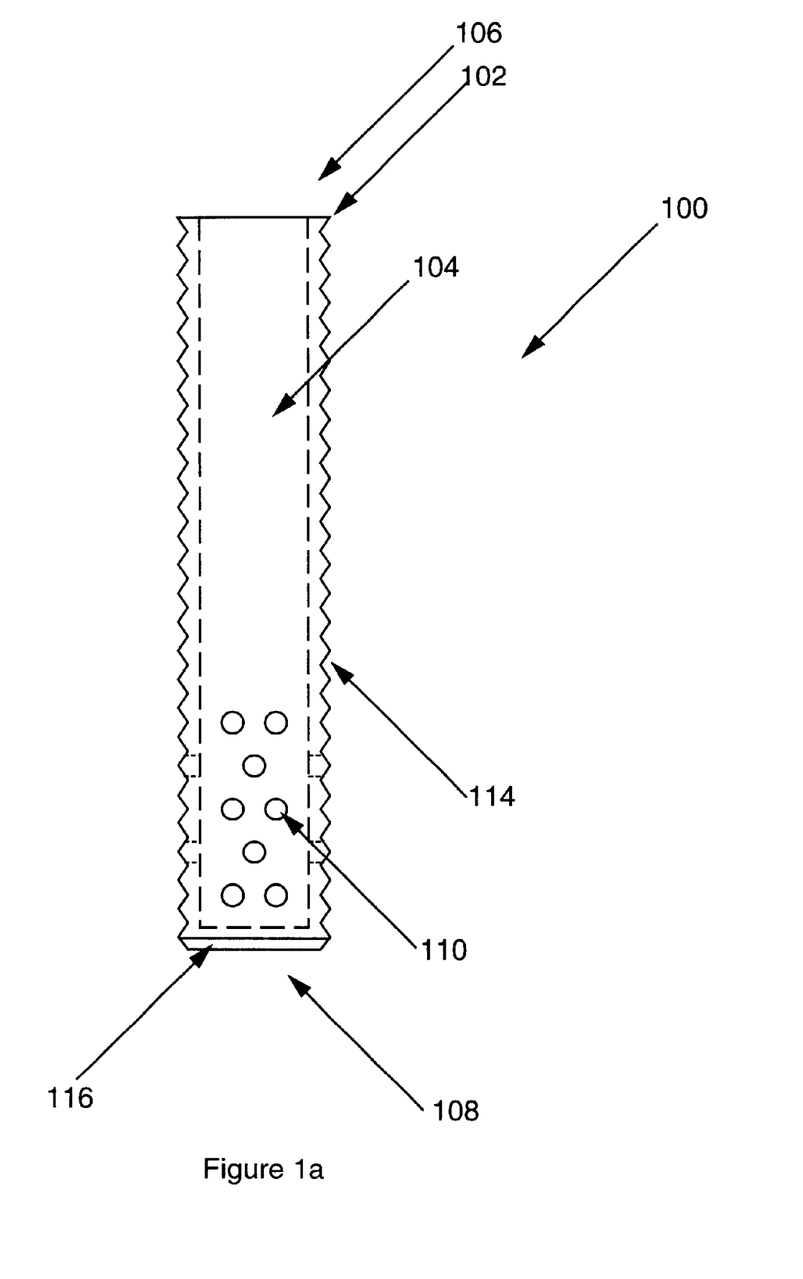
FIGS. 1a, 1b and 1c illustrate a cannula of an embodiment of the present invention, with FIG. 1a showing a side view of the cannula, FIG. 1b showing a cannula applicator of an embodiment of the present invention, and FIG. 1c showing a side view of the cannula engaged with the cannula applicator.
Figure 1B:
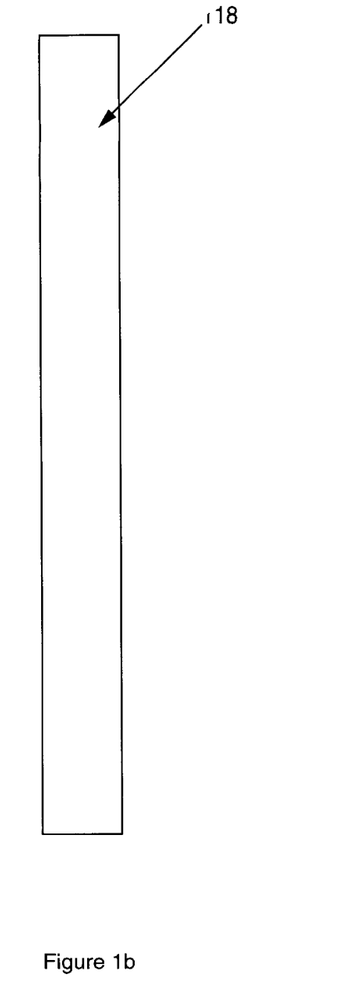
Figure 1C:
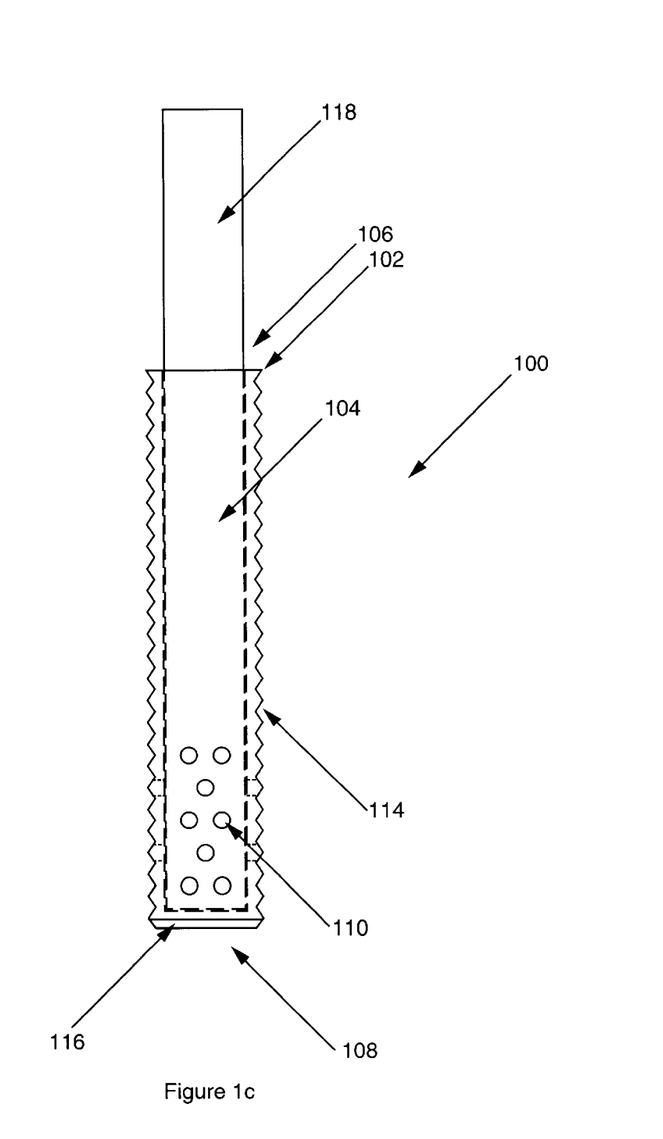

Referring now to FIGS. 1a, 1b and 1c, a cannula 100 of the present invention is shown, with FIG. 1a showing a side view of the cannula 100, FIG. 1b showing a cannula applicator 118 of the present invention, and FIG. 1c showing a side view of the cannula 100 engaged with the cannula applicator 118. The cannula 100 has an elongated cylindrical body 102 with a central bore 104, the body 102 having a proximal end 106 providing access to the bore 104 (especially access by a cannula applicator 118, plunger 200, syringe 300 and drill bit 318 of the present invention, as illustrated in other figures and as described in greater detail below), and a distal end 108 that is perforated with holes 110 as shown. The outer surface of the cannula 100 is threaded with outer threads 114 for engagement with inner threads of a tapped drill hole and to restrict proximal migration of the bone cement, as described in greater detail below, and for other reasons. The cannula 100 should be formed from biocompatible material (e.g., poly methyl methacrylate) inasmuch as it will become incarcerated into the target vertebral body in accordance with the procedures described herein.

For example in the illustrated embodiment, the body 102 of the cannula 100 has a length of 70.0 mm, an inner diameter of 4 mm, and an outer diameter of 6.5 mm. It should be understood that the cannula 100 can have other dimensions without departing from the scope of the present invention. For example, in some applications, a useful outer diameter would be 5.5 mm, 7.5 mm, or any measurement between 5.5 mm and 7.5 mm, and any other measurement less than 5.5 mm, or greater than 7.5 mm, as needed depending on the clinical application for which the invention is used, and the corresponding dimensions of the other instruments used with the cannula 100. For another example, in some applications, a useful cannula length would be shorter or longer than 70.0 mm, as necessary or desirable depending on the depth of the drill hole. The illustrated embodiment has a cannula 100 with a body length of 70.0 mm, inner diameter of 4.0 mm, and outer diameter of 6.5 mm. An inner diameter of 4.0 mm, while not required, is useful for minimizing resistance to flow of the bone cement, as described in greater detail below.

Further preferably, the cannula 100 has a radiodense tip 116 that can be used to aid the surgeon in determining the position of the cannula 100 after the cannula 100 has been placed into the target vertebral body. While any radiodense material or configuration can be used to make the tip 116 radiodense, suitable examples include using metal, wires, beads or barium. Any method know in the art for determining the position of a radiodense mass in a vertebral body can be used to determine the position of the radiodense tip 116 in the target vertebral body.

Referring again to FIGS. 1b and 1c, a cannula applicator 118 of the invention is shown, alone in FIG. 1b and in FIG. 1c engaged with the cannula 100. The applicator 118 has an elongated cylindrical body and is used to assist the surgeon in threading the cannula 100 into a tapped drill hole (e.g., by providing structural support for the cannula 100 and allowing purchase of the cannula 100 so that the cannula 100 can be twisted into position) and in determining the placement of the cannula 100 in the vertebral body, as described in greater detail below, and for other purposes. Accordingly, the applicator 118 is dimensioned so that it can be placed into and removed from the proximal end 106 of the cannula 100 and so that when the applicator 118 is placed into the bore 104 of the cannula 100, it fits snugly within the bore 104 as shown. For example in the illustrated embodiment, the diameter of the applicator 118 is 4.0 mm and its length is 100.0 mm. The intimate fit enables the applicator 118 to provide structural support for the cannula 100 as the cannula 100 is twisted into the drill hole, and causes the applicator 118 to grip the walls of the bore 104 so that cannula 100 will rotate when the applicator 118 is rotated, so that the cannula 100 will threaded into the drill hole.

Also preferably, the applicator 118 comprises a radiodense material or is of a radiodense configuration, so that it can be used to determine the position of the cannula 100 as the cannula 100 is threaded into the drill hole. While any radiodense material or configuration can be used to make the applicator 118, suitable examples include using metal or barium. Any method know in the art for determining the position of a radiodense mass in a vertebral body can be used to determine the position of the applicator 118 in the target vertebral body.

Figure 2A:
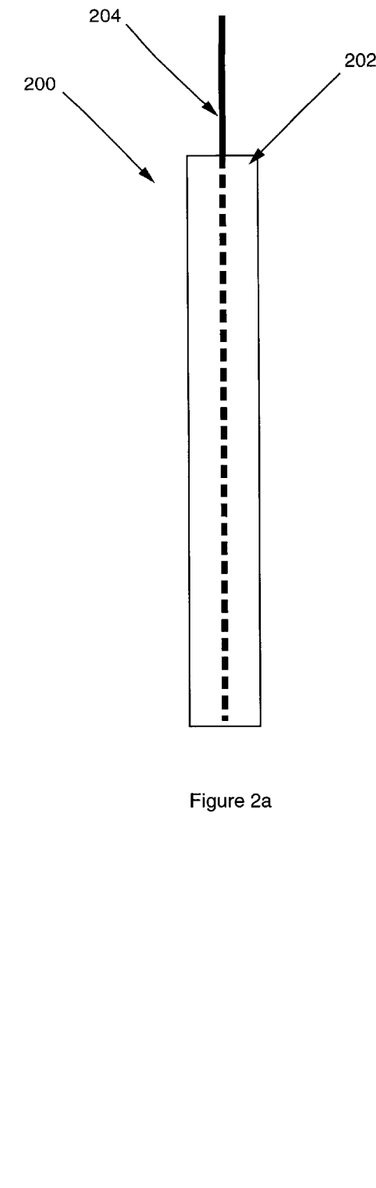
FIGS. 2a and 2b illustrate a plunger of an embodiment of the present invention, with FIG. 2a showing the plunger alone and FIG. 2b showing the cannula of FIG. 1a engaged by the plunger.
Figure 2B:
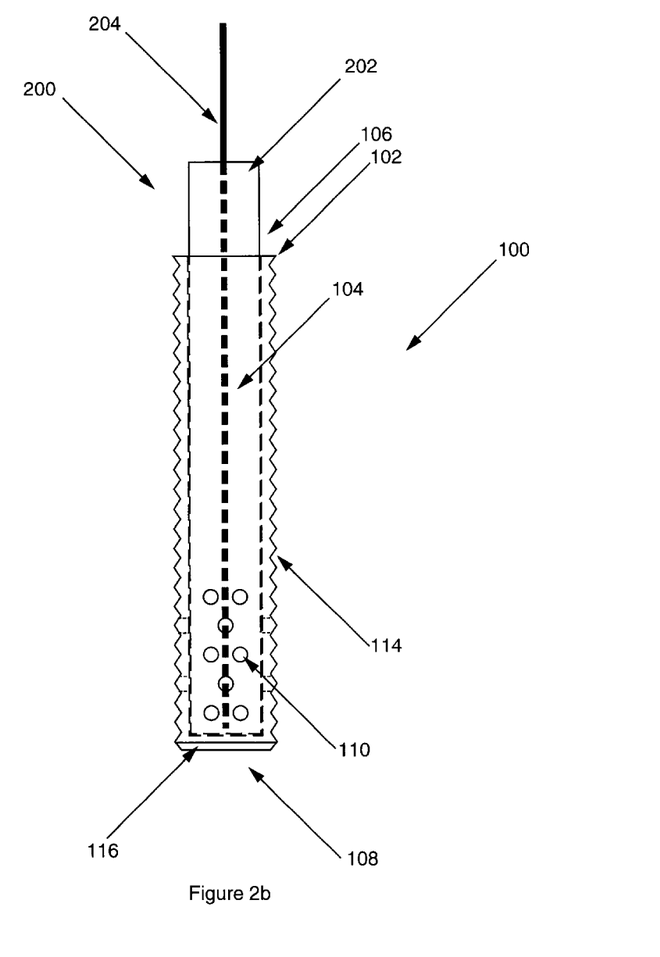

Referring now to FIGS. 2a and 2b, a plunger 200 of the present invention is shown, with FIG. 2a showing the plunger 200 alone and FIG. 2b showing the cannula 100 engaged by the plunger 200. The plunger 200 has an elongated cylindrical body 202 that fits tightly within the bore 104 of the cannula 100 so that it can be used to squeeze bone cement out the holes 110 in the distal end 108 of the cannula 100 as described in greater detail below. For example in the illustrated embodiment, the body 202 has a length of 80.0 mm and a diameter of 4.0 mm. Preferably, the body 202 is formed from a material that is softer than the biocompatible material from which the body 102 of the cannula 100 is formed. As described in greater detail below, this difference in material facilitates the drilling away of the plunger 200 after it is used to distribute the bone cement. Also preferably, the plunger 200 is formed from biocompatible material (e.g., poly methyl methacrylate), as some of the plunger 200 may remain after most of the plunger 200 has been drilled away, and the remaining portion would become incarcerated in the vertebral body. Also preferably, the body 202 has a central longitudinal axis and an internal guide wire 204 (such as, for example, a k wire) or guide rod passing through the central longitudinal axis. As described in greater detail below, this guide wire 204 also facilitates the drilling away of the plunger 202.

Figure 3A:
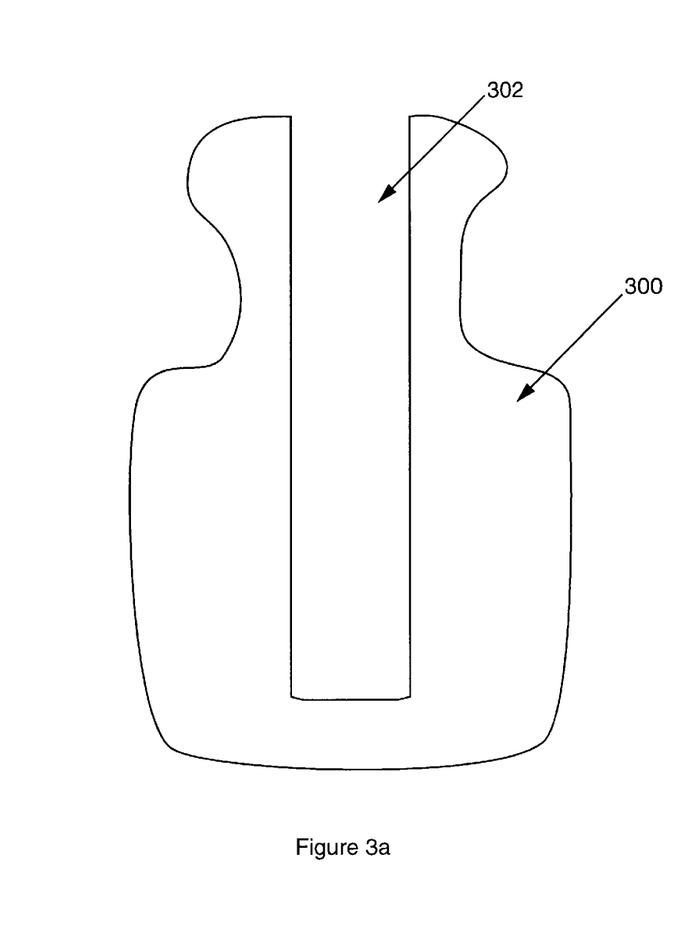
FIGS. 3a–f illustrate a method of an embodiment of the present invention, with FIGS. 3a–b illustrating the drilling and tapping of a hole in a target vertebral body, FIG. 3c illustrating the placement of the cannula of FIG. 1a in the hole, FIGS. 3d–e illustrating the filling of the cannula bore with bone cement, and the distribution of the bone cement out the holes in the distal end of the cannula using the plunger of FIG. 2a, and FIG. 3f illustrating the drilling out of the plunger body from the cannula bore using the guide wire in the plunger as a guide.

A use of the invention will now be described with reference to FIGS. 3a–f. As illustrated in FIG. 3a, upon proper preparation of the target vertebral body or bodies in accordance with known and accepted surgical procedures, the surgeon drills a hole 302 in the target vertebral body 300, typically using drill bits of increasing diameter (e.g., starting with a 2.5 mm diameter bit and ending with a 4.0 mm diameter bit, in preparation for tapping the hole with a 5.25 mm diameter tap).

Figure 3B:
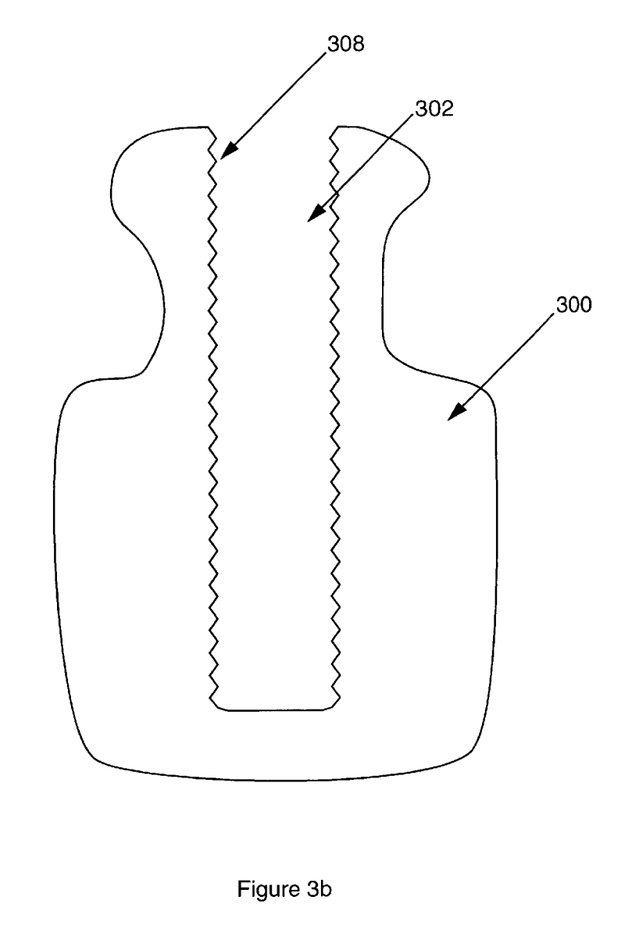

Then, as illustrated in FIG. 3b, the surgeon threads the hole 302 using a tap in a manner known in the art, establishing threads 308 on the walls of the hole 302. Preferably, a plurality of taps are provided, so that the surgeon can choose from taps with, for example, 5.25 mm, 6.25 mm or 7.25 mm diameters, depending on the size of cannula that the surgeon is planning to use for a particular patient. (For many applications, the use of a tap that is 0.25 mm diameter smaller than the cannula to be used is preferred.) Typically, during the preparation of the tapped hole 302, the surgeon will use a probe to determine the proper angulation and depth of the hole 302. The surgeon repeats the above procedure for each hole 302 he plans to drill.

Figure 3C:
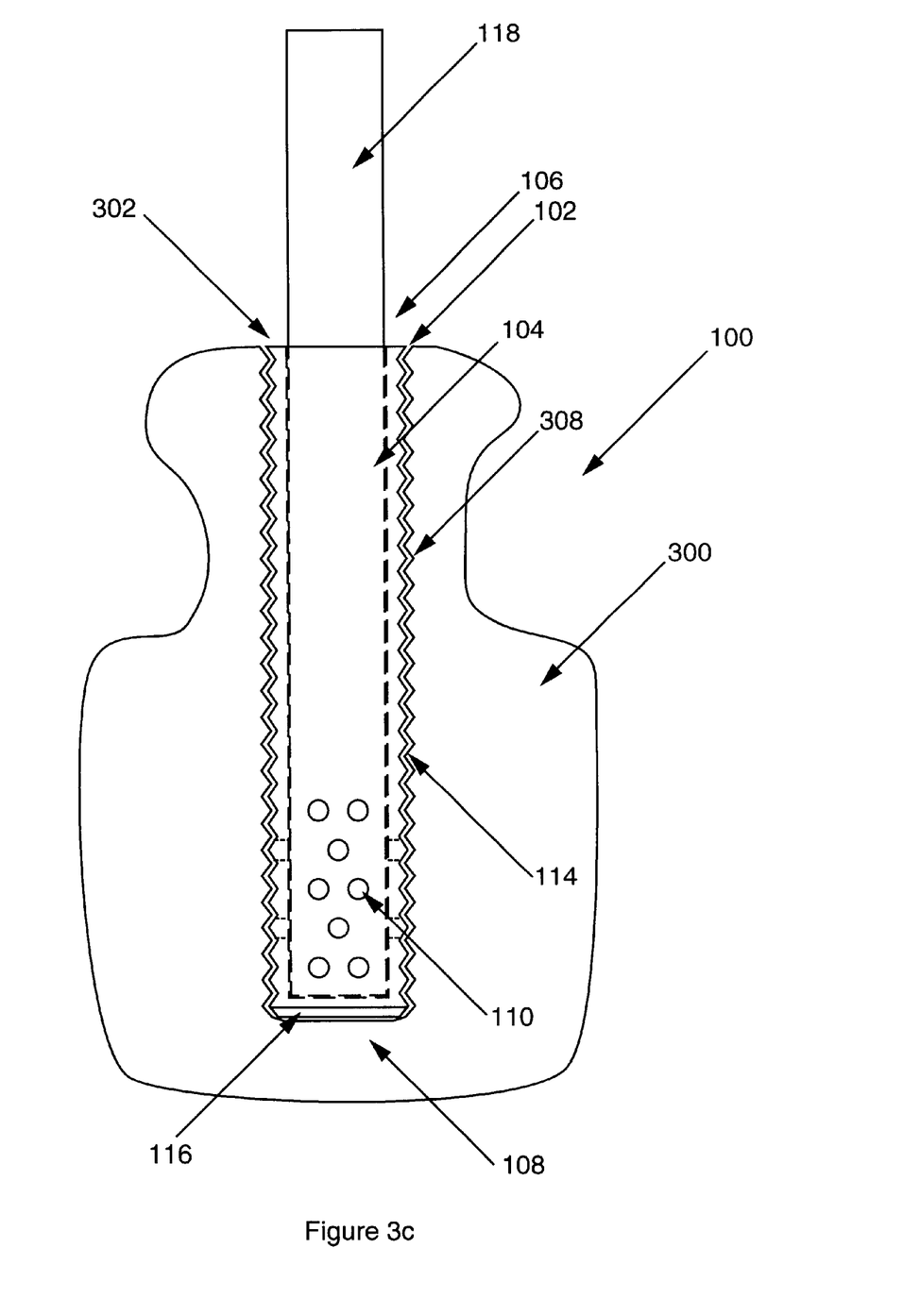

Next, as illustrated in FIG. 3c, the surgeon inserts into the hole 302 a cannula 100 of the present invention, using an appropriately sized cannula applicator 118 of the present invention. The surgeon inserts the applicator 118 into the proximal end 106 of the cannula 100 and into the bore 104 of the cannula 100, establishing a tight fit of the applicator 118 against the walls of the bore 104. It should be noted that the applicator 118 may already be inserted into the bore 104 before the surgeon is provided with the cannula 100, so that procedural steps to be made by the surgeon can be minimized. Once the applicator 118 is fitted into the bore 104, the surgeon places the cannula 100 into the tapped hole 302, and repeatedly turns the applicator 118 to rotate the cannula 100 so that the outer threads 114 of the cannula 100 engage the threads 308 of the hole 302 and the cannula 100 is twisted deeper into the hole 302 to the desired position (typically, all the way into the hole 302). The intimate fit of the applicator 118 against the walls of the bore 104 facilitates the rotation of the cannula 100 in response to the rotation of the applicator 118. The structural integrity of the applicator 118, in conjunction with the intimate fit of the applicator 118 in the bore 104, provides structural support for the thin-walled cannula 100 as the cannula 100 is twisted into position. Inasmuch as the applicator 118 is preferably radiodense, the surgeon is able to assess the position of the cannula 100 in a manner known in the art as needed until he is satisfied that the cannula 100 has been placed in the desired position. For each drilled hole 302, the surgeon places a cannula 100 of the present invention into the drilled hole 302 using an appropriately sized applicator 118 in accordance with the above procedure. The surgeon should leave each applicator 118 in place until it is time to inject the bone cement, as described below. This will keep bleeding to a minimum and will continue to make possible radiographic assessments of the position of each applicator 118 and accordingly each cannula 100.

Figure 3D:
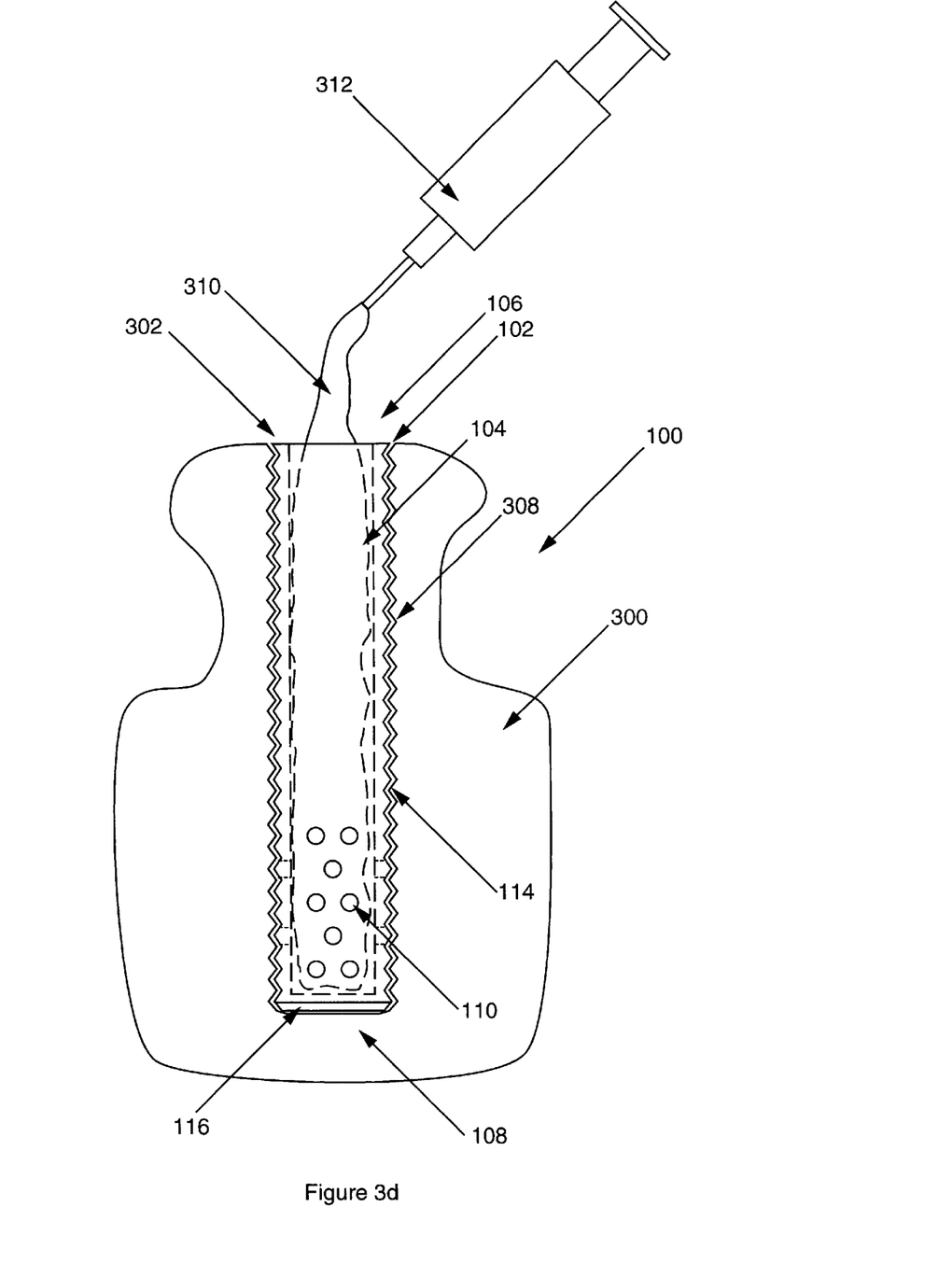
Figure 3E:
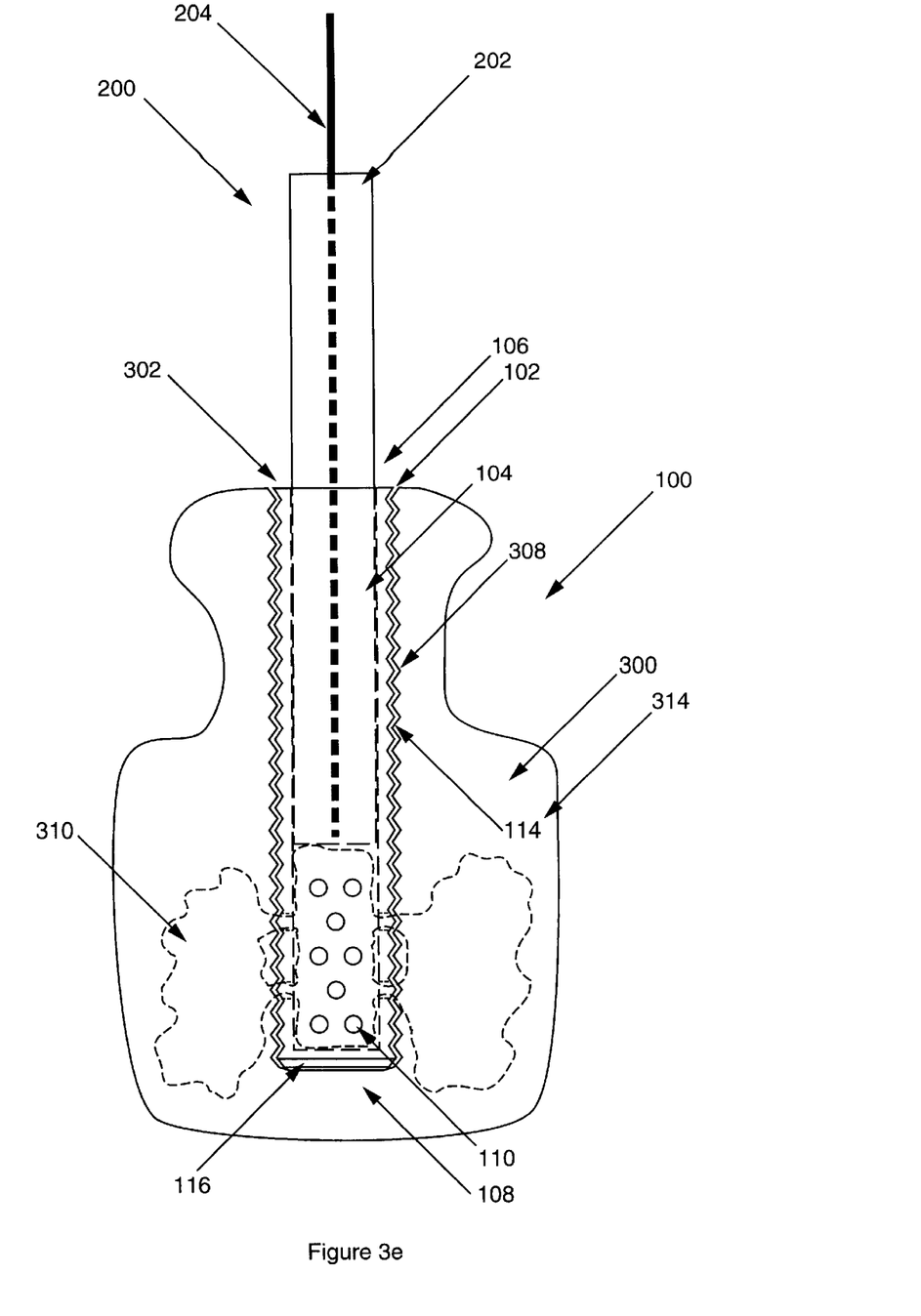

As illustrated in FIGS. 3d–e, once each drilled hole 302 has been fitted with a cannula 100 of the present invention, the surgeon prepares the appropriate bone cement mixture 310 and loads one or more syringes 312 with the bone cement 310, in a manner know in the art. Then, for each installed cannula 100, one at a time, the surgeon removes the applicator 118, injects an appropriate amount of the bone cement 310 into the bore 104 using the syringe(s) 312, and applies a plunger 200 of the present invention to distribute the bone cement 310 through the holes 110 of the distal end 108 of the cannula 100. FIG. 3d illustrates the injection of the bone cement 310 into the cannula bore 104. FIG. 3e illustrates the distribution of the bone cement 310 using the plunger 200. Typically, the appropriate amount of bone cement will be 1.5 cc to 2.0 cc of cement per hole. In order to effect this procedure for each cannula 100, the surgeon first removes the applicator 118 from the cannula 100 by pulling it from the bore 104. The engagement of the threads 114 of the cannula 100 with the threads 308 of the drilled hole 302 prevent the cannula 100 from also being removed. Next, the surgeon prepares the bone cement 310, loads the syringe(s) 312, and injects the bone cement 310 into the cannula bore 104. Then, the surgeon inserts an appropriately sized plunger 200 of the present invention into the proximal end 106 of the cannula 100 and into the cannula bore 104, pushing the plunger 200 down the bore 104 so that the bone cement 310 squeezes out the holes 110 at the distal end 108 of the cannula 100 and into the bone 314 surrounding the cannula 100. The engagement of the outer threads 114 of the cannula 100 with the inner threads 308 of the drilled hole 302 limit the migration of bone cement 310 out of the drilled hole 302 during the distribution process. For each cannula 100, the surgeon leaves the plunger 200 in until each plunger 200 has been applied and the bone cement 310 has set in the surrounding bone 314. The setting of the bone cement 310 in the surrounding bone 314 strengthens the surrounding bone 314 in preparation for the next steps, which involve re-tapping the target vertebral body for a bone screw.

Figure 3F:
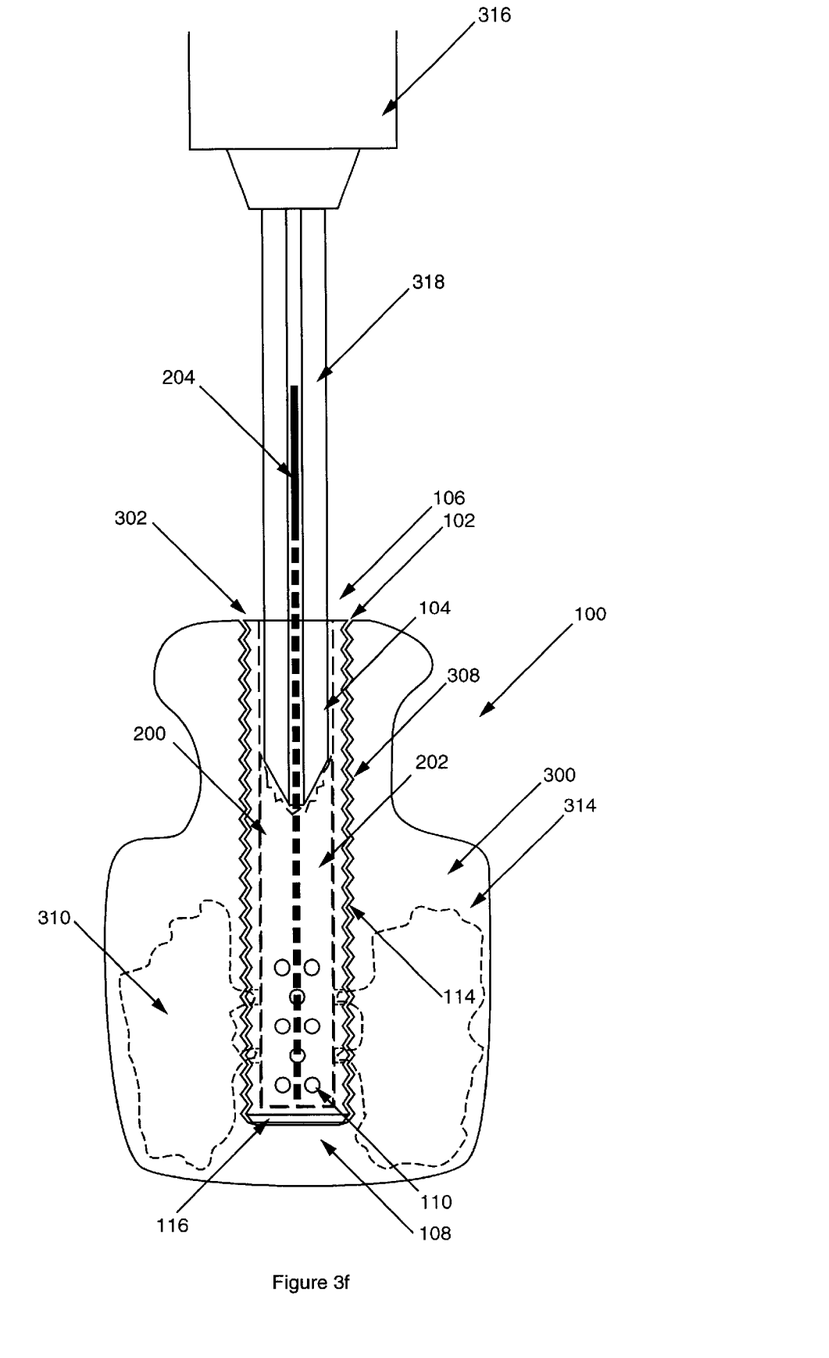

As illustrated in FIG. 3f, once each plunger 200 has been applied and the distributed bone cement has set, the surgeon drills out each plunger 200 using a drill 316 and cannulated drill bit 318. The surgeon selects a cannulated drill bit 318 having an appropriate outer diameter (preferably, the outer diameter of the drill bit 318 has the same diameter as the diameter of the cannula bore 104 which in the illustrated embodiment is 4.0 mm), sets the drill bit 318 into the drill 316, passes the drill bit 318 over the guide wire 204 extending from the plunger 200, and proceeds to drill into the plunger body 202, following the guide wire 204 to ensure that only the plunger body 202 material (and in some applications part, e.g., 05.mm, of the cannula 100) is being drilled away. As noted above, the preferable softness of the plunger body 202 relative to the cannula body 102 facilitates the drilling away of primarily the plunger body 202. The surgeon repeats this procedure for each installed cannula 100.

Finally, the surgeon threads each hole that remains after each plunger 200 has been removed, using a tap in a manner known in the art. Typically, a tap having a diameter of 5.5 mm to 7.5 mm will be useful, preferably matching the diameter of the cannula 100 that has been used. A tap suitable for use in the illustrated embodiment would have a diameter of 6.5 mm. Once each new hole has been tapped, the surgeon can insert a bone screw of the surgeon's choice into each hole, and complete the operation.

While there has been described and illustrated specific embodiments of an intervertebral spacer device, it will be apparent to those skilled in the art that variations and modifications are possible without deviating from the broad spirit and principle of the present invention. The invention, therefore, shall not be limited to the specific embodiments discussed herein.

I claim:

1. A system for reinforcing bone in preparation for screw implantation, comprising:
   a cannula comprising a central longitudinal bore into which uncured bone cement is receiveable, the cannula further comprising a proximal end having a proximal opening longitudinally communicating with the central bore of the cannula, the cannula further comprising a distal end having at least one distal opening communicating with the central bore of the cannula and through which uncured bone cement is distributeable;
   a cannula applicator engageable with the cannula and by which the cannula is placeable into a hole in a bone; and
   a plunger longitudinally translatable in the central bore of the cannula and by which untaxed bone cement is pushable in the central bore of the cannula;
   wherein the plunger comprises a drillable material and an internal central longitudinal guide wire by which drilling of the plunger by a cannulated drill bit is facilitated.

2. The system of claim 1, wherein the cannula further comprises a longitudinal axis, the system comprising the cannula applicator by which the cannula is structurally supportable and rotatable about the longitudinal axis.

3. The system of claim 2, wherein the central bore of the cannula has at least one wall and the cannula applicator intimately fits in the central bore of the cannula and frictionally engages the at least one wall of the central bore of the cannula when fitted therein.

4. The system of claim 2, wherein the cannula comprises a threaded outer surface by which the cannula is threadable into a tapped hole in a bone.

5. The system of claim 1, wherein the cannula applicator comprises a radiodense portion.

6. The system of claim 1, wherein the cannula comprises a radiodense portion.

7. The system of claim 1, wherein the cannula comprises a biocompatible material.

8. The system of claim 1, wherein the cannula comprises poly methyl methacrylate.

9. The system of claim 1, wherein the plunger comprises a biocompatible material.

10. The system of claim 1, wherein the plunger comprises poly methyl methacrylate.

11. The system of claim 1, wherein the plunger is softer than the cannula.

12. A system for reinforcing bone in preparation for screw implantation, comprising:
    a cannula comprising a central longitudinal bare into which uncured bone cement is receiveable, the cannula further comprising a proximal end having a proximal opening longitudinally communicating with the central bore of the cannula, the cannula further comprising a distal end having at least one distal opening communicating with the central bore of the cannula and through which uncured bone cement is distributeable;
    a cannula applicator engageable with the cannula and by which the cannula is placeable into a hole in a bone; and
    a plunger longitudinally translatable in the central bore of the cannula and by which uncured bone cement is pushable in the central bore of the cannula;
    wherein the cannula further comprises a longitudinal axis, the system comprising the cannula applicator by which the cannula is structurally supportable and rotatable about the longitudinal axis;
    wherein the central bore of the cannula has at least one wall and the cannula applicator intimately fits in the central bore of the cannula and frictionally engages the at least one wall of the central bore of the cannula when fitted therein.

13. The system of claim 12, wherein the cannula comprises a threaded outer surface by which the cannula is threadable into a tapped hole in a bone.

14. The system of claim 12, wherein the cannula applicator comprises a radiodense pardon.

15. The system of claim 12, wherein the cannula comprises a radiodense portion.

16. The system of claim 12, wherein the cannula comprises a biocompatible material.

17. The system of claim 12, wherein the cannula comprises poly methyl methacrylate.

18. The system of claim 12, wherein the plunger comprises a biocompatible material.

19. The system of claim 12, wherein the plunger comprises poly methyl methacrylate.

20. The system of claim 12, wherein the plunger is softer than the cannula.

* * * * *

UNITED STATES PATENT AND TRADEMARK OFFICE
CERTIFICATE OF CORRECTION

PATENT NO. : 6,752,809 B2
DATED : June 22, 2004
INVENTOR(S) : Josef E. Gorek

It is certified that error appears in the above-identified patent and that said Letters Patent is hereby corrected as shown below:

Column 1,
Line 11, "canulated" should read -- cannulated --.
Line 26, "trijoint" should read -- tri-joint --.

Column 2,
Line 7, "methy" should read -- methyl --.

Column 6,
Line 40, "threaded" should read -- thread --.

Column 9,
Line 20, "untaxed" should read -- uncured --.

Column 10,
Line 5, "bare" should read -- bore --.
Line 34, "pardon" should read -- portion --.

Signed and Sealed this

Twenty-eighth Day of September, 2004

JON W. DUDAS
*Director of the United States Patent and Trademark Office*